(12) United States Patent
Willard et al.

(10) Patent No.: US 9,801,631 B2
(45) Date of Patent: Oct. 31, 2017

(54) SHEATH AND BALLOON TENSIONER AND LOCATOR SYSTEMS AND METHODS

(71) Applicant: St. Jude Medical Puerto Rico LLC, Caguas, PR (US)

(72) Inventors: Steven Willard, Bloomington, MN (US); Martha Escobar, Jordan, MN (US); Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 730 days.

(21) Appl. No.: 13/778,408

(22) Filed: Feb. 27, 2013

(65) Prior Publication Data

US 2014/0135822 A1    May 15, 2014

Related U.S. Application Data

(60) Provisional application No. 61/726,418, filed on Nov. 14, 2012.

(51) Int. Cl.
| | |
|---|---|
| *A61B 17/08* | (2006.01) |
| *A61M 25/06* | (2006.01) |
| *A61B 17/00* | (2006.01) |
| *A61B 90/00* | (2016.01) |

(52) U.S. Cl.
CPC .............. *A61B 17/08* (2013.01); *A61B 90/03* (2016.02); *A61M 25/0662* (2013.01); *A61B 17/0057* (2013.01); *A61B 17/00491* (2013.01); *A61B 2017/0065* (2013.01); *A61B 2017/00557* (2013.01); *A61B 2017/00601* (2013.01); *A61B 2017/00654* (2013.01); *A61B 2090/064* (2016.02)

(58) Field of Classification Search
CPC .......... A61B 17/00491; A61B 17/0057; A61B 2017/00575; A61B 2017/00615; A61B 2017/00659; A61B 2017/00672
See application file for complete search history.

(56) References Cited

U.S. PATENT DOCUMENTS

| | | | |
|---|---|---|---|
| 3,532,095 A * | 10/1970 | Miller ................ | A61B 18/1402 606/45 |
| 4,368,730 A | 1/1983 | Sharrock | |
| RE40,863 E * | 7/2009 | Tay .................... | A61B 17/0057 606/50 |
| 8,333,787 B2 | 12/2012 | Pipenhagen et al. | |

(Continued)

FOREIGN PATENT DOCUMENTS

| | | |
|---|---|---|
| EP | 2384708 A1 | 11/2011 |
| WO | 2011079620 A1 | 7/2011 |

OTHER PUBLICATIONS

U.S. Appl. No. 13/770,586, filed Feb. 19, 2013.

(Continued)

*Primary Examiner* — Thomas McEvoy
(74) *Attorney, Agent, or Firm* — Holland & Hart

(57) ABSTRACT

A tissue closure system includes a sheath and a tissue closure device. The sheath includes a tensioner assembly. The tissue closure device is insertable through and connected to the sheath, and includes an expandable member positionable distal of a distal end of the sheath. Operating the tensioner assembly applies a biasing force to the tissue closure device that withdraws the expandable member.

19 Claims, 8 Drawing Sheets

(56) References Cited

U.S. PATENT DOCUMENTS

| | | |
|---|---|---|
| 8,506,592 B2 | 8/2013 | Killion et al. |
| 2008/0214316 A1* | 9/2008 | Jacob et al. ................. 464/145 |
| 2008/0312666 A1* | 12/2008 | Ellingwood ....... A61B 17/0057 |
| | | 606/142 |
| 2010/0211000 A1* | 8/2010 | Killion et al. ................. 604/57 |
| 2011/0166595 A1 | 7/2011 | Vidlund et al. |
| 2011/0282383 A1 | 11/2011 | Vidlund et al. |
| 2012/0323175 A1* | 12/2012 | Vogelbaum et al. ...... 604/95.04 |
| 2013/0006299 A1 | 1/2013 | Pipenhagen et al. |
| 2013/0190808 A1 | 7/2013 | Tegels et al. |
| 2013/0190812 A1 | 7/2013 | Vidlund |
| 2013/0190813 A1 | 7/2013 | Tegels et al. |

OTHER PUBLICATIONS

U.S. Appl. No. 13/770,714, filed Feb. 19, 2013.
U.S. Appl. No. 13/772,834, filed Feb. 21, 2013.
U.S. Appl. No. 13/773,062, filed Feb. 21, 2013.
U.S. Appl. No. 13/773,206, filed Feb. 21, 2013.
PCT Notification of Transmittal of the International Search Report and the Written Opinion of the International Searching Authority, or the Declaration for PCT International Application No. PCT/US2013/027841, mailed Jul. 22, 2013 (11 pp.).

* cited by examiner

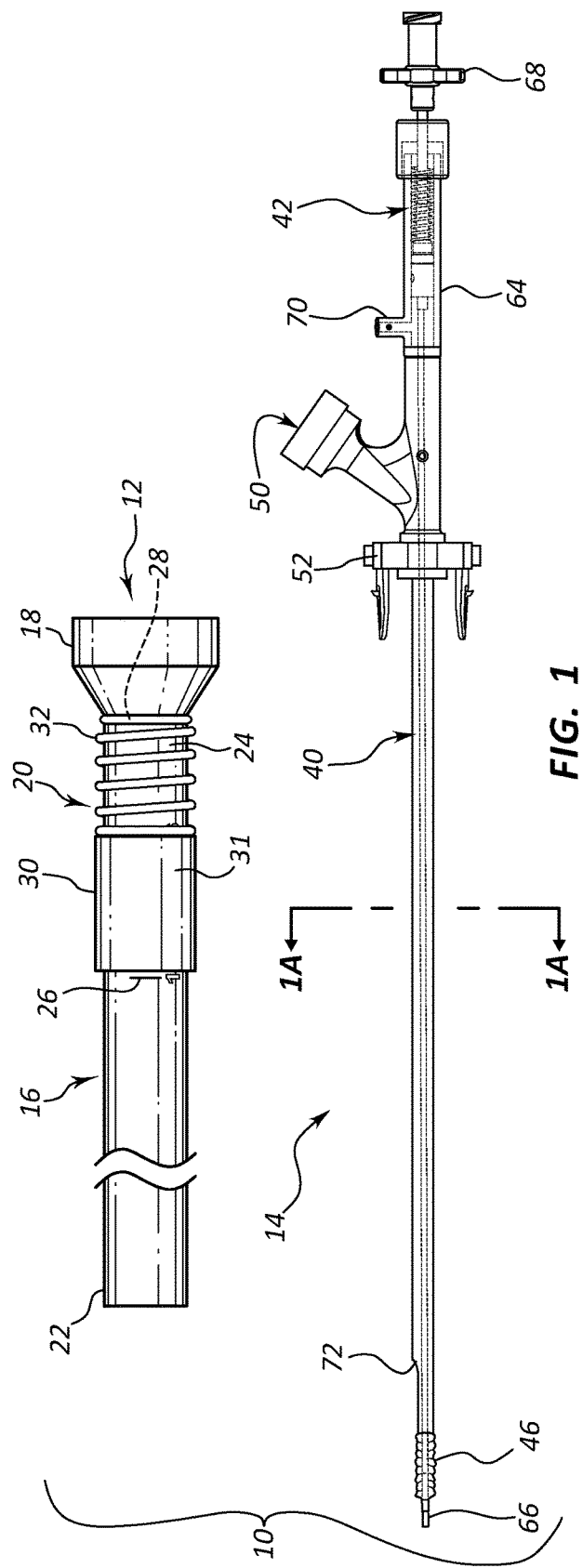
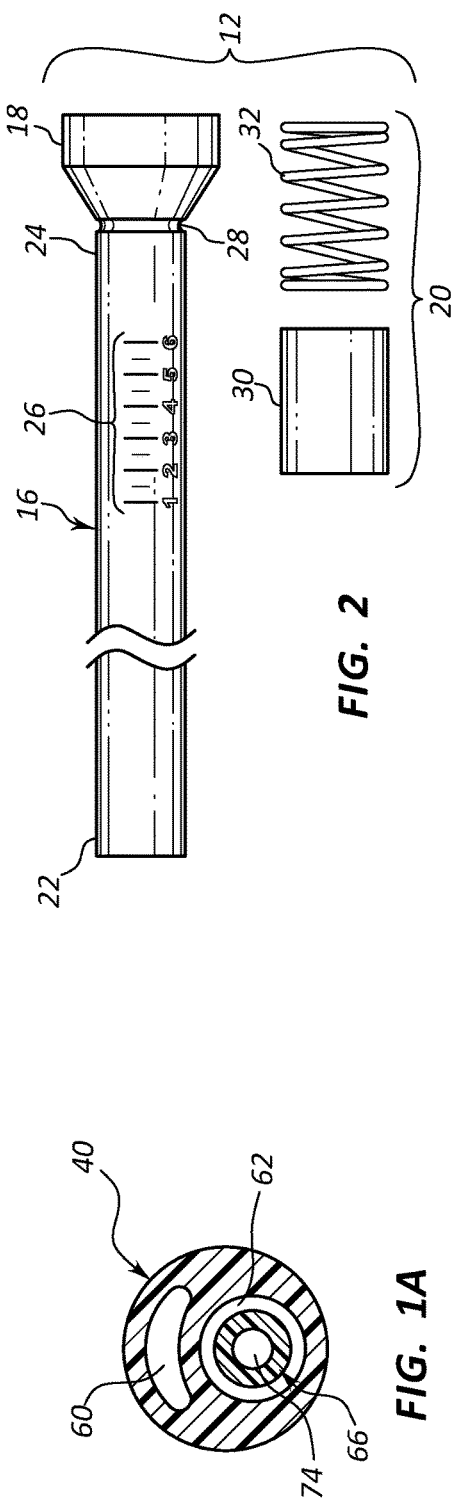
FIG. 1
FIG. 1A
FIG. 2

SHEATH AND BALLOON TENSIONER AND LOCATOR SYSTEMS AND METHODS

CROSS-REFERENCE TO RELATED APPLICATION

This application claims the benefit of the filing date of U.S. Provisional Application No. 61/726,418, filed Nov. 14, 2012, and entitled SHEATH AND BALLOON TENSIONER AND LOCATER SYSTEMS AND METHODS, the disclosure of which is incorporated, in its entirety, by reference.

TECHNICAL FIELD

The present disclosure relates generally to accessing tissue punctures, and more particularly, to methods and systems for controlling dimensions of a sheath that is insertable through the tissue puncture.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one aspect of interest in the ability to access the puncture prior to closing the puncture. An insertion sheath is commonly inserted into the puncture to create an access port for the closure device used to close the puncture. An expandable structure such as an inflatable balloon is inserted through the insertion sheath and positioned within the vessel where the expandable structure is used to temporarily seal the puncture. Opportunities exist for accessing the puncture and temporarily sealing the puncture as part of a puncture closure procedure.

SUMMARY

One aspect of the present disclosure relates to an insertion sheath for use with a tissue closure system. The insertion sheath includes a sheath shaft having a central lumen, a hub connected to a proximal end of the sheath shaft, and a tensioner assembly. The tensioner assembly includes a biasing member positioned on the sheath shaft and having distal and proximal end portions, and a handle member connected to the distal end portion of the biasing member. Applying an axial force to the handle member against a biasing force exerted by the biasing member moves the sheath shaft axially.

The biasing member may include a compression spring. The biasing member may include a boot structure. The biasing member may include a polymer material. The proximal end portion of the biasing member may be connected to the hub. The handle member may include a transparent material. The sheath shaft may include indices on an outer surface thereof against which axial movement of the handle member is measured. The proximal end portion of the biasing member may be fixed relative to one of the sheath shaft and the hub. The handle member may include a lip configured to apply an axial force to the handle member.

Another aspect of the present disclosure relates to a method of locating a tissue puncture through a tissue layer. The method includes providing an insertion sheath and a balloon catheter, wherein the insertion sheath includes a tensioner assembly and the balloon catheter includes an expandable portion. The method also includes inserting the insertion sheath into the tissue puncture, inserting the balloon catheter through the insertion sheath, expanding the expandable portion, and applying a variable withdrawal force to the balloon catheter with the tensioner assembly to draw the expandable portion against an inner surface of the tissue layer adjacent to the tissue puncture to locate the tissue puncture.

The tensioner assembly may include a handle portion and a biasing member, and applying the variable withdraw force includes moving the handle portion proximally against biasing forces of the biasing member. The handle portion and biasing member may be positioned along an exterior of the insertion sheath, and moving the handle portion includes sliding the handle portion along the insertion sheath.

The expandable portion may include an inflation balloon, and expanding the expandable portion includes delivering inflation fluid to the inflation balloon. Inserting the balloon catheter may include positioning the expandable portion distal of a distal end of the insertion sheath. The insertion sheath may include a sheath shaft and a hub, the hub being connected to a proximal end of the sheath shaft, and the tensioner assembly including a biasing member positioned on the sheath shaft abutting against the hub. The sheath shaft may include indices on an outer surface thereof, and a position of a portion of the tensioner assembly relative to the indices indicates a tension force applied by the expandable member to the tissue layer.

Another aspect of the present disclosure relates to a method of sealing a puncture in a vessel. The method includes providing an insertion sheath and a tissue closure device, wherein the insertion sheath includes a tensioner assembly and the tissue closure device includes an expandable balloon member. The method includes inserting the insertion sheath and tissue closure device into the puncture, connecting the insertion sheath and tissue closure device together, expanding the balloon member within the vessel, and applying a withdrawal force to the sheath with the tensioner assembly to draw the expanded balloon into contact with the vessel adjacent to the puncture.

The tensioner assembly may include a handle portion and a biasing member, and applying the withdrawal force includes moving the handle portion axially against biasing forces of the biasing member to move the insertion sheath axially. The method may include maintaining the withdrawal force while delivering a sealant to the tissue puncture with the tissue closure device. The method may include releasing the withdrawal force, retracting the balloon, and withdrawing the tissue closure device through the sealant.

Another aspect of the present disclosure relates to a tissue closure system that includes a sheath and a tissue closure device. The sheath includes a tensioner assembly. The tissue closure device is insertable through and connected to the sheath, and includes an expandable member positionable distal of a distal end of the sheath. Operating the tensioner assembly applies a biasing force to the tissue closure device that withdraws the expandable member.

The tensioner assembly may include a handle and a biasing member, and operating the tensioner assembly includes moving the handle proximally against biasing forces exerted by the biasing member. The expandable member may be positionable through a tissue puncture and expanded to temporarily seal the tissue puncture from a position distal of the tissue puncture upon operating the tensioner assembly.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example tissue closure system in accordance with the present disclosure.

FIG. 1A is a cross-sectional view of a tissue closure device of the tissue closure system of FIG. 1 taken along cross-section indicators 1A-1A.

FIG. 2 is an exploded side view of a sheath of the tissue closure system of FIG. 1.

Throughout the drawings, identical reference numbers designate similar, but not necessarily identical, elements.

DETAILED DESCRIPTION

Figure 3:
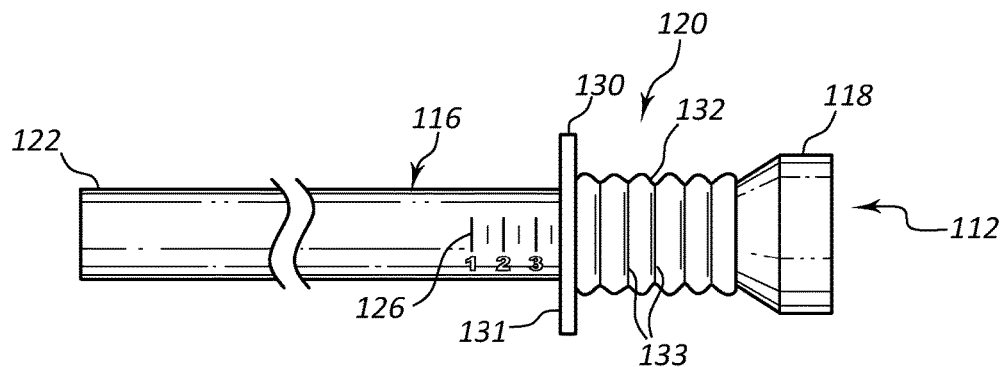
FIG. 3 is a side view of another example sheath in accordance with the present disclosure.

The apparatuses and methods disclosed herein may be used to access percutaneous punctures made through a body layer of a patient to gain access to a body cavity. Access through a percutaneous puncture allows a physician to carry out various procedures in or through the body cavity for examination, surgery, treatment and the like. While not meant to be limiting, the systems are illustrated being used to access percutaneous punctures in blood vessels in patients for various procedures. It will be appreciated that the apparatuses and methods are applicable to other procedures requiring access to a puncture through body tissue into a cavity including, for example, laparoscopic surgery and other microscopic surgery techniques using a relatively small incision. Applications of access apparatuses and methods including those implementing principles described herein include access of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

An exemplary embodiment of the present disclosure includes a sheath for use with a tissue closure system. The sheath is insertable through a tissue puncture to gain access to the tissue puncture and provide an unobstructed path for insertion of a tissue closure device through the sheath to the tissue puncture. Typically, the sheath and tissue closure device are connected together so that withdrawing the sheath also withdraws the tissue closure device.

The tissue closure device may include an expandable member such as an inflatable balloon at a distal end thereof. The expandable member is positioned distal of a distal end of the sheath. The expandable member is expanded on a distal side of the tissue puncture. Withdrawing the expanded expandable member against the tissue adjacent to the tissue puncture temporarily seals the tissue puncture and provides an anchoring function. The temporary seal provided by the expanded expandable member is typically maintained while delivering a sealant to seal closed the tissue puncture on a proximal side of the tissue puncture.

The sheath may include a tensioning assembly, which when operated applies a variable withdrawal force to the tissue closure device to help maintain an appropriate level of withdrawal force on the expanded expandable member. The appropriate level of withdrawal force typically is sufficient to maintain the temporary seal by contact of the expanded expandable member against the inner surface of the tissue adjacent to the tissue puncture while avoiding excessive withdrawal forces that would pull the expanded expandable member through the tissue puncture.

The tensioner assembly may include a handle portion and a biasing member. The operator typically applies a withdrawal force to the handle portion, which moves the handle portion against biasing forces of the biasing member. The biasing member acts as a buffer between the forces applied to the handle by the operator portion and the tissue closure device (e.g., the expanded expandable member). A distance the handle portion is withdrawn proximally against the biasing forces of the biasing member may correlate to a withdrawal force that is applied to the tissue closure device. A distance the handle portion is moved may be tracked along a shaft of the sheath by the operator to give the operator a visual indication of the amount of withdrawal force being applied to the tissue closure device.

In one example, the sheath includes a sheath shaft, a hub, and the tensioner assembly described above. The tensioner assembly may include a handle portion slideable along a length of the sheath shaft. The biasing member is interposed between the handle portion and the hub. In some examples, a proximal portion of the biasing member may be attached to the hub or fixed relative to the hub and sheath shaft. A plurality of indices may be positioned along an exterior surface of the sheath shaft. Moving the handle portion relative to the indices may provide a visual indication to the operator of the distance the handle portion has moved along the sheath shaft. The distance the handle moves may correlate to a withdrawal force that is being applied to the tissue closure device that is connected to the sheath (e.g., connected via the hub). Applying an axial force to the handle member against a biasing force exerted by the biasing member moves the tissue closure device and thereby moves the expandable member.

The tensioner assembly may operate to apply a variable withdrawal force to the tissue closure device that draws the expanded expandable member of the tissue closure device against an inner surface of the tissue layer adjacent to the tissue puncture to help locate and temporarily seal the tissue puncture. The tensioner assembly may operate to apply a withdrawal force to the sheath that draws the expanded expandable member into contact with the tissue (e.g., vessel) adjacent to the tissue puncture. Another aspect involves operating the tensioner assembly to apply a biasing force to the tissue closure device that withdraws the expandable member.

Referring now to FIGS. 1-2, an example tissue closure system 10 is shown including a sheath 12 and a tissue closure device 14. The tissue closure device 14 may also be referred to as a balloon catheter or a tissue puncture closure device. The tissue closure device 14 is inserted through the sheath 12 as part of treating a patient (e.g., sealing a tissue puncture). The tissue closure device is typically connected to the sheath 12 so that the sheath 12 and tissue closure device 14 move in tandem once connected together.

Sheath 12 includes a sheath shaft 16, a hub 18, and a tensioner assembly 20. The sheath shaft 16 includes a plurality of indices 26 along an outer surface thereon (see FIG. 2). The sheath shaft 16 has distal and proximal ends 22, 24. Hub 18 is mounted at a proximal end of sheath shaft 16. Hub 18 may include a retention groove 28.

Tensioner assembly 20 may include a handle portion 30 and a biasing member 32. The tensioner assembly 20 may be positioned on an outer surface of the sheath shaft 16. In other arrangements, at least portions of tensioner assembly 20 are positioned within or operable within the sheath shaft 16 and hub 18. In some arrangements, a tensioner assembly 20 may be interposed between sheath 12 and tissue closure device 14.

Handle portion 30 is slideable along at least a portion of a length of sheath shaft 16. As handle portion 30 moves axially, the indices 26 are exposed for viewing by the operator. The biasing member 32 typically is interposed between handle portion 30 and hub 18. Biasing member 32 may be connected to hub 18 at the retention groove 28. A proximal end portion of the biasing member 32 may be connected directly to hub 18. In other arrangements, a portion of biasing member 32 may be connected or fixed to sheath shaft 16.

Handle portion 30 may include a gripping surface 31. The gripping surface 31 may be ergonomically designed for easy grasping by thumbs or fingers of the operator. In some arrangements, gripping surface 31 is configured for grasping by the operator and applying a withdrawal or proximally directed force to handle portion 30.

Biasing member 32 may include a spring such as a compression spring. The spring may apply a constant biasing force during a compression cycle. Alternatively, the spring may apply a variable biasing force (e.g., an increasing biasing force) during a compression cycle. The biasing member 32 may be connected to handle portion 30. In one example, biasing member 32 is co-molded with handle portion 30 so as to be permanently connected thereto. The biasing member 32 may be interchanged with other biasing members having different properties for use in different procedures.

The tissue closure device 14 may include an inflation tube 40, a balloon location device 42, an inflation source 44 (see FIGS. 5-10), a balloon 46, a sealant source 48 (see FIGS. 8-9), a sealant manifold 50, and a sheath connector 52. The inflation tube 40 may include a sealant lumen 60 and an inflation lumen 62 (see FIG. 1A). The sealant lumen 60 may include a distal opening 72. A flowable sealant may be delivered from the sealant source 48 and through the sealant manifold 50 and sealant lumen 60 where the sealant is expelled at the distal opening 72 at a location adjacent to a tissue puncture as will be described in further detail below.

The balloon location device 42 includes a housing 64, an inner tube 66, an inner tube manifold 68, and an inflation port 70. The inner tube 66 is configured to extend through the inflation lumen 62 (see FIG. 1A). The inner tube 66 may include an inner tube lumen 74 (see FIG. 1A). A secondary sealant source 49 (see FIGS. 9 and 10) may be connected to the inner tube manifold 68. The inflation source 44 may be connected to the inflation port 70 for delivery of a volume of inflation fluid to the balloon 46 via the inflation lumen 62.

The balloon 46 may be connected to the inflation tube 40 at a proximal end, and a distal end of the balloon 46 may be connected to the inner tube 66 of the balloon location device 42. Inflating or expanding the balloon 46 may move the inner tube 66 relative to the housing 64 thereby providing a visual indicator to the operator of an inflation condition of the balloon 46.

The sheath connector 52 may be fixed relative to the inflation tube 40 and sealant manifold 50 of the tissue closure device 14. Sheath connector 52 may be inserted into the hub 18 of sheath 12 and provide a positive connection there between. In some arrangements, sheath connector 52 provides a permanent connection between sheath 12 and tissue closure device 14. In other arrangements, sheath connector 52 is configured to provide a releasable connection between sheath 12 and tissue closure device 14. Typically, inserting tissue closure device 14 a distance required to connect sheath connector 52 to hub 18 also positions balloon 46 and a distal opening 72 of sealant lumen 60 distal of the distal end 22 of sheath 12.

When sheath connector 52 is connected to hub 18, any movement of sheath shaft 16 and hub 18 in a distal or proximal direction concurrently moves the tissue closure device 14 in the same distal or proximal direction. Sheath 12 and tissue closure device 14 may move in tandem (e.g., in fixed axial movement relative to each other).

Figure 4:
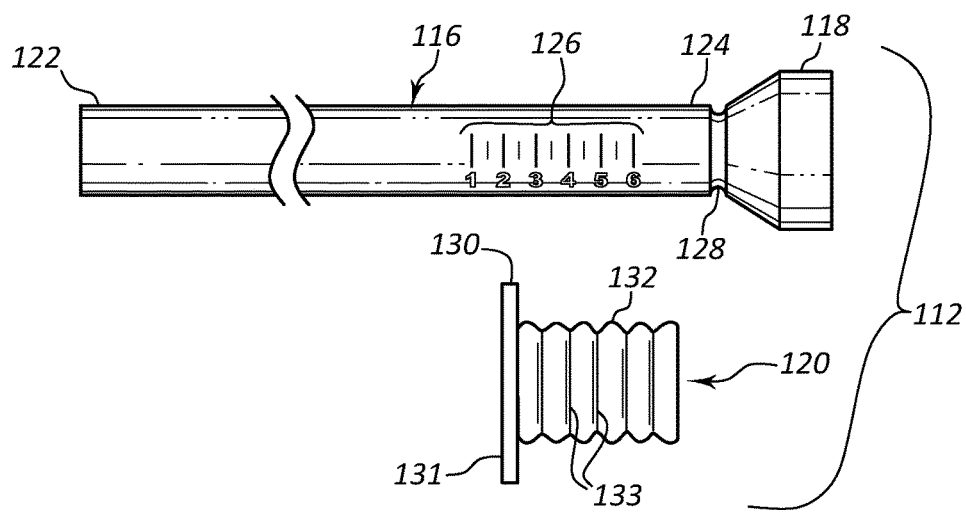
FIG. 4 is an exploded side view of the sheath of FIG. 3.

Referring now to FIGS. 3 and 4, another example sheath 112 is shown including a sheath shaft 116, a hub 118 and a tensioner assembly 120. The sheath shaft 116 includes distal and proximal ends 122, 124 and a plurality of indices 126 positioned along an outer surface thereof. Hub 118 includes a retention groove 128. Tensioner assembly 120 includes a handle portion 130 and a biasing member 132.

The handle portion 130 may have a different structure than the handle portion 30 shown and described with reference to FIGS. 1 and 2. Handle portion 130 may include a lip 131 or other surface upon which an operator may apply a proximally directed withdrawal force to handle portion 130. Handle portion 130 may be connected to biasing member 132 at a distal end of biasing member 132. A proximal end of biasing member 132 may be connected to either sheath shaft 116 or hub 118. In one example, a proximal end portion of biasing member 132 is connected to hub 118 at the retention groove 128.

Biasing member 132 may have a boot or billow-type construction. Biasing member 132 may have a generally continuous construction between its proximal and distal ends. Biasing member 132 may include open distal and proximal ends to permit biasing member 132 to slide over sheath shaft 116.

Biasing member 132 may comprise polymer materials such as, for example, silicone. Biasing member 132 may include a plurality of pre-folds, creases, bends or compression lines 133. Biasing member 132 may be configured to apply a consistent or variable biasing force when compressed.

Other types of biasing member constructions may be possible. For example, leaf springs, coil springs, extension springs, shape member materials, and elastic materials are just some of the options available for a biasing member that provides the desired cushioning and controlled application of tension force during use of the tissue closure system.

Figure 5:
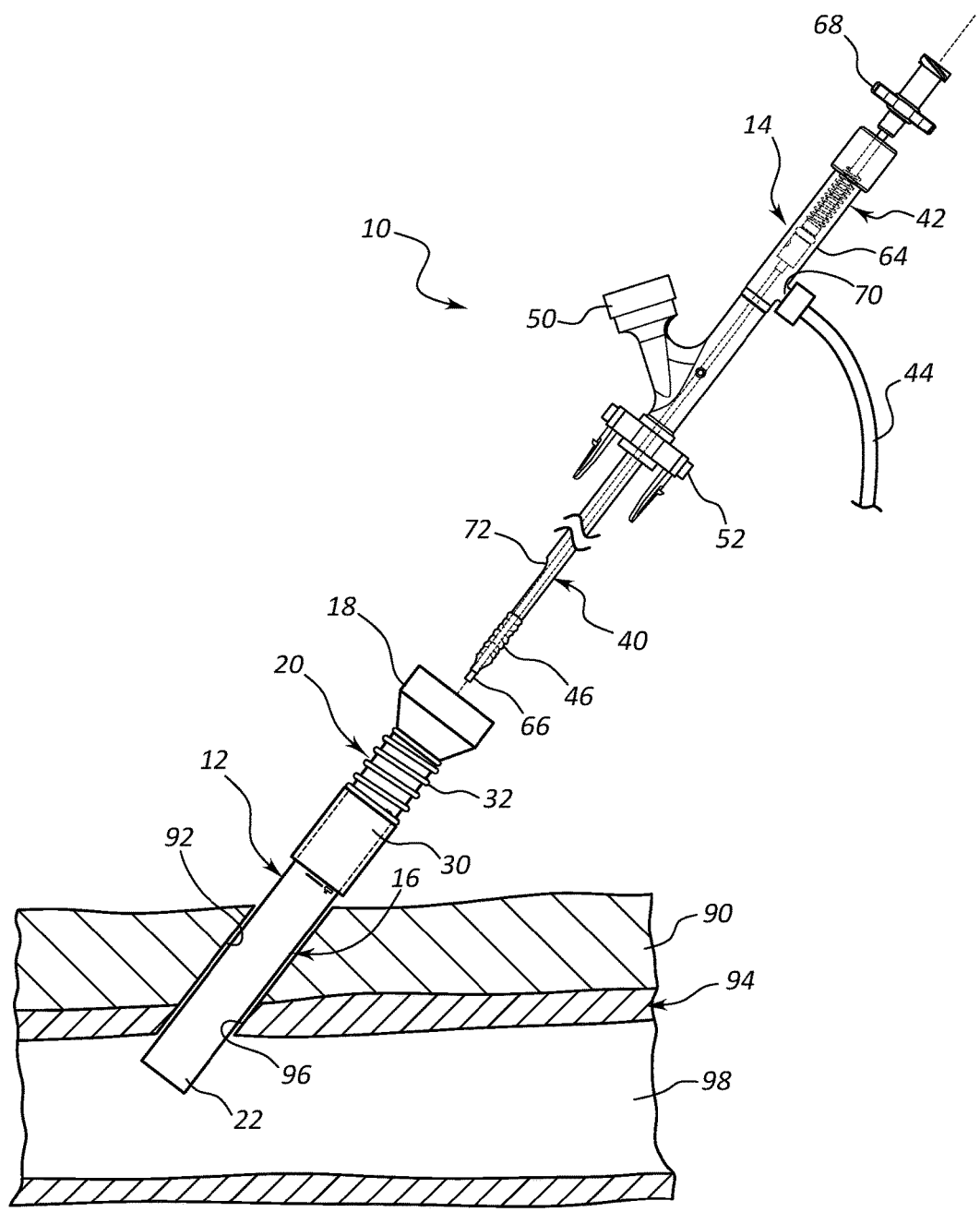
FIGS. 5-10 illustrate steps of sealing a tissue puncture using the tissue closure system of FIG. 1.
Figure 6:
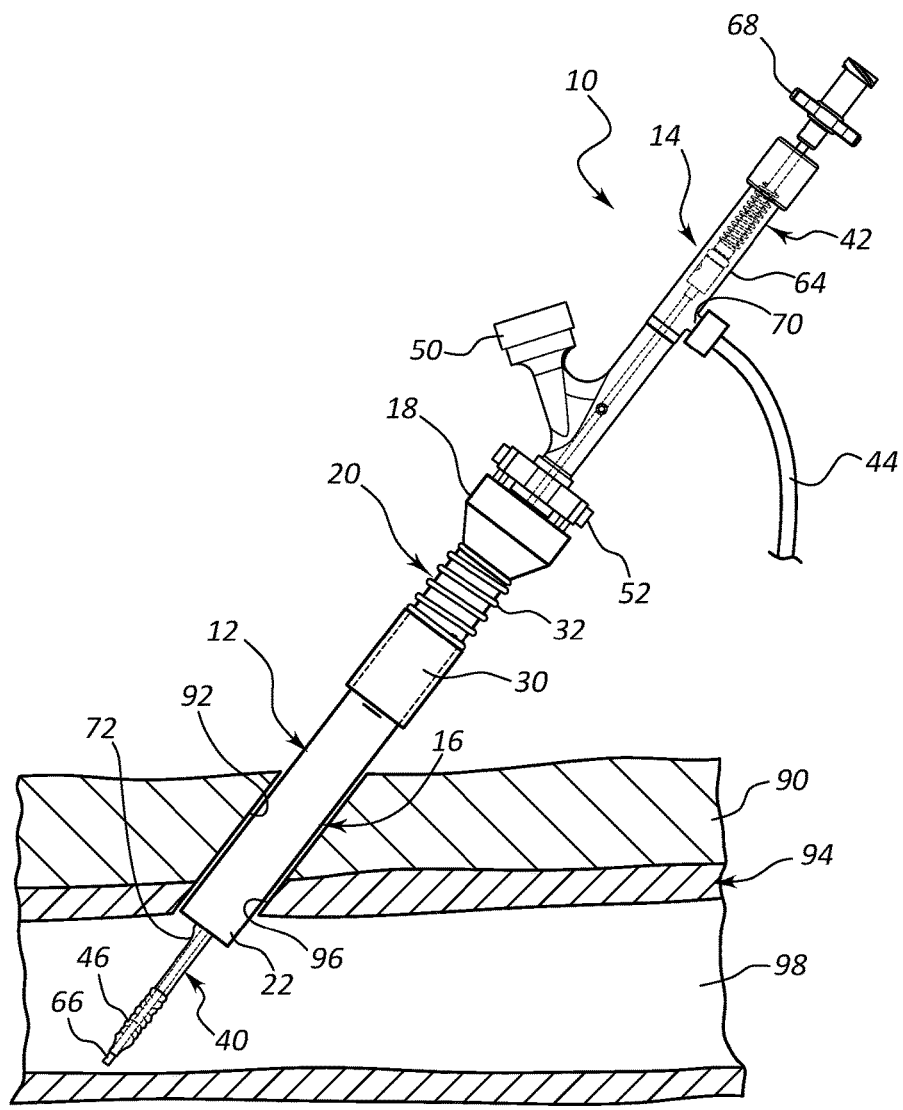

Referring now to FIGS. 5-10, an example method of sealing a tissue puncture using the tissue closure system 10 is shown and described. FIG. 5 shows the sheath 12 inserted through a tissue tract 92 of a tissue layer 90 and a vessel puncture 96 of a vessel 94 to gain access to a vessel interior 98. The tissue closure device 14 is aligned with an opening in hub 18 and prepared for insertion through sheath 12 and into the vessel interior 98. FIG. 6 shows the tissue closure device 14 inserted through sheath 12 to position balloon 46 and distal opening 72 distal of the distal end 22 of sheath 12.

Figure 7:
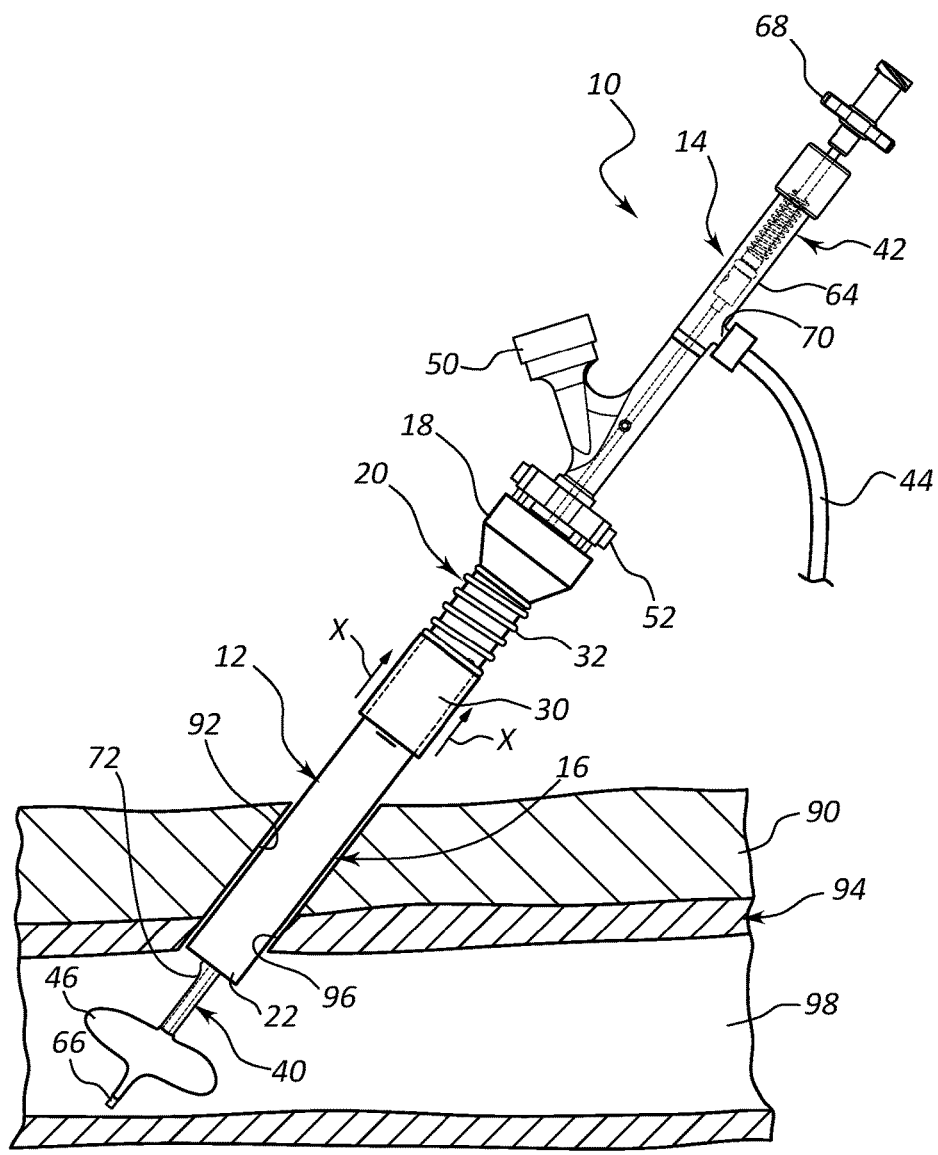
Figure 8:
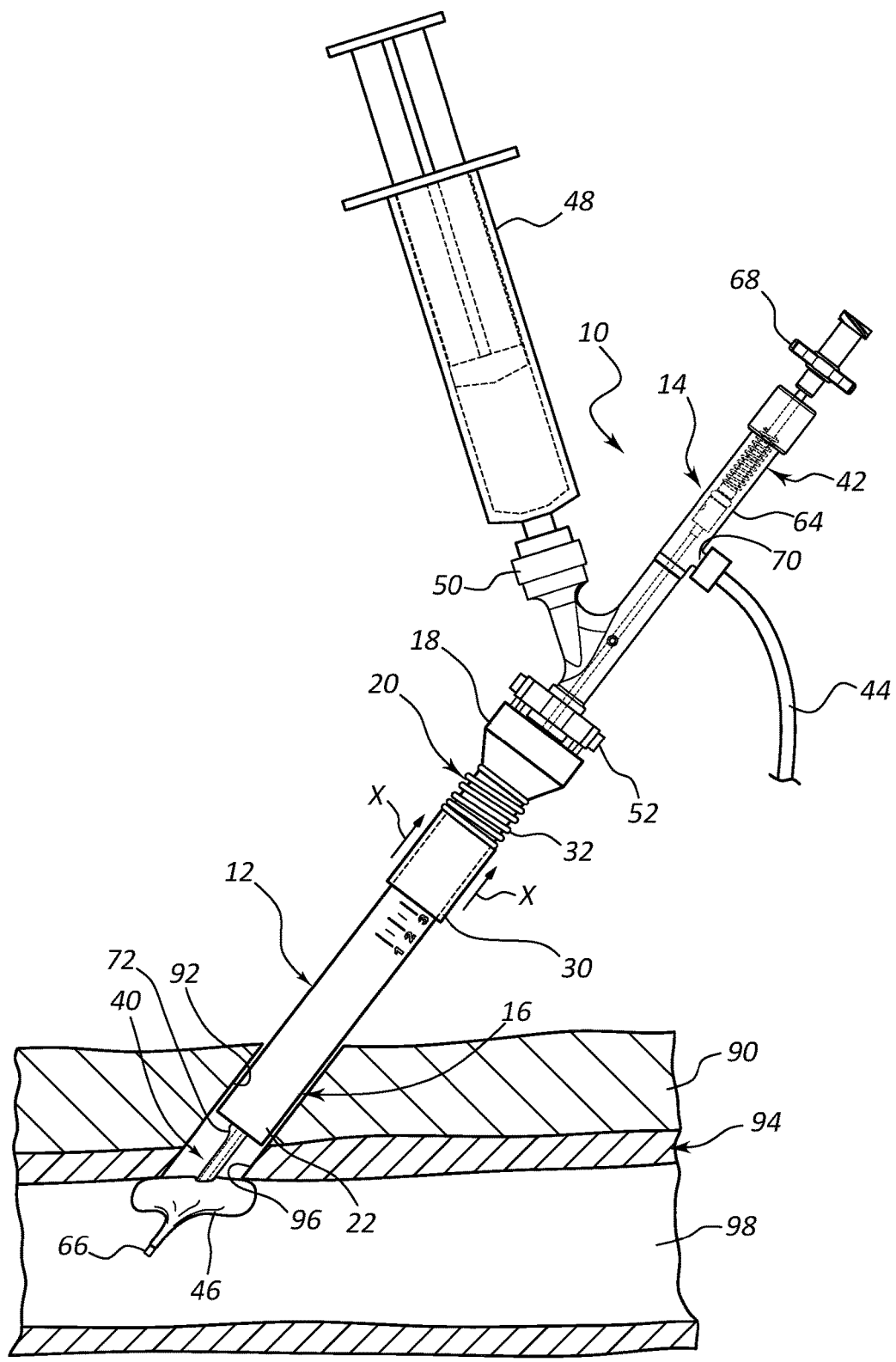

Referring to FIG. 7, a volume of inflation fluid is delivered from inflation source 44 and through the tissue closure device 14 to inflate balloon 46. With the balloon 46 inflated, the operator grasps the handle portion 30 and applies a withdrawal force in the X direction. The handle portion 30 moves against biasing forces applied by biasing member 32. Because the sheath 12 and tissue closure device 14 are connected together with the sheath connector 52, any movement of sheath shaft 16 and hub 18 resulting from application of the withdrawal force to handle portion 30 also moves the tissue closure device 14 in the proximal direction. The withdrawal force is maintained on the handle portion 30 until balloon 46 contacts an inner surface of vessel 94 adjacent to vessel puncture 96 as shown in FIG. 8. The handle portion 30 may be moved proximally until some of the indices 26 are visible. The indices 26 indicate to the operator that a certain amount of tension or withdrawal force is being applied to balloon 46.

Figure 9:
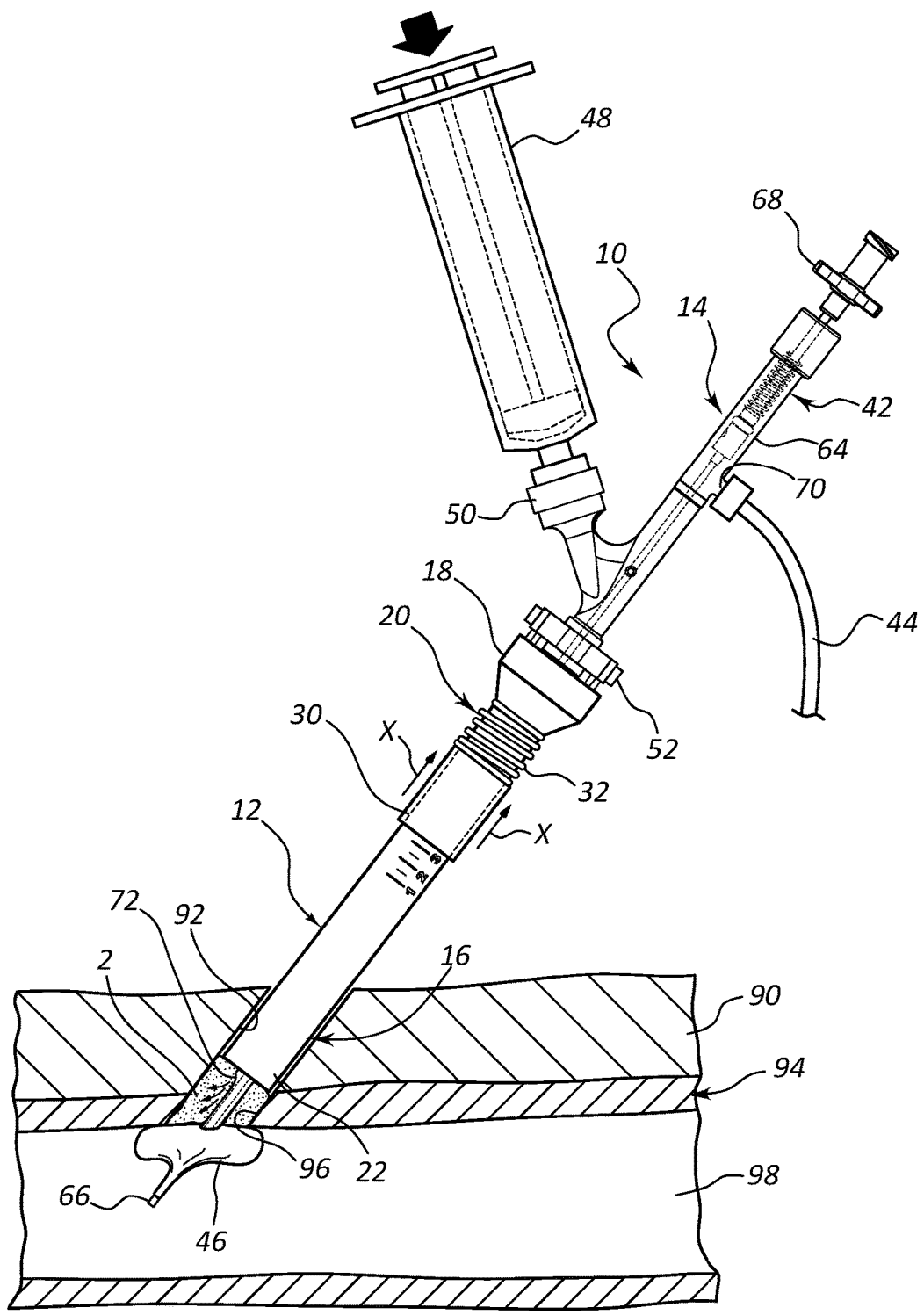

The operator maintains the handle portion 30 in the desired position relative to sheath shaft 16 as shown by the indices 26 while a volume of sealant is delivered from sealant source 48 through the distal opening 72 and into the tissue tract 92 and vessel puncture 96 as shown in FIG. 9. The sealant delivered to the tissue tract 92 and vessel puncture 96 forms into a sealant plug 2. The withdrawal force may be maintained on the handle portion 30 to maintain the temporary seal provided by balloon 46 until the sealant plug 2 is sufficiently solidified to limit movement of the sealant material into vessel interior 98 when the balloon 46 is deflated.

Figure 10:
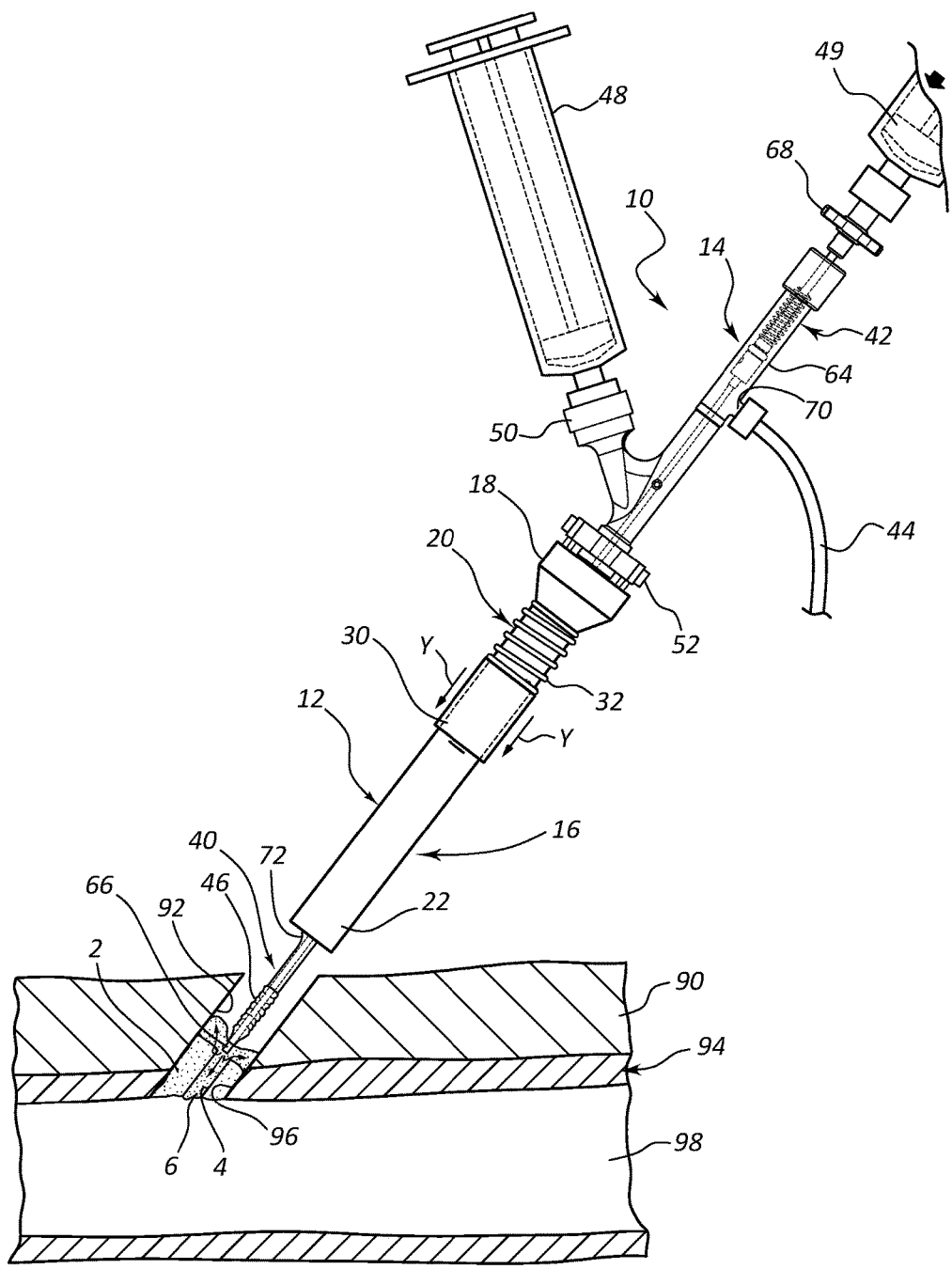

Referring to FIG. 10, the operator releases handle portion 30 to release the tension of inflated balloon 46 against the inner surface of vessel 94. Balloon 46 is deflated and tissue closure device 14 is withdrawn through sealant plug 2. Withdrawing the tissue closure device 14 may leave behind a sealant tract 4 within sealant plug 2. In some arrangements, the tissue closure device 14 may be configured to deliver an additional volume of sealant to seal sealant tract 4. The additional volume of sealant may be delivered via the secondary sealant source 49 and through inner tube 66 to sealant tract 4 as shown in FIG. 10. In other arrangements, a detachable tip (not shown) carried by inner tube 6 may be lodged within sealant tract 4. In still further examples, an additional volume of sealant may be delivered through the distal opening 72 and into tissue tract 92 to further seal tissue tract 92 and vessel puncture 96.

The tensioner assemblies 20, 120 are shown and described herein with reference to a mounting on sheath 12, 112. Other configurations are possible in which tensioner assembly 20 is positioned at other locations. In one example, the tensioner assembly may be positioned on a portion of the tissue closure device, such as, for example, on the sealant manifold 50 or on the balloon location device 42. If the sheath 12 and tissue closure device 14 are connected together so as to move in tandem axially (e.g., via a connection of sheath connector 52 to hub 18), then the handle portion of the tensioner assembly may be positioned at any desired location along a length of the sheath 12 and tissue closure device 14. In one example, the balloon location device 42 is fixed axially relative to the sealant manifold 50, and the tensioner assembly 20 is mounted to the housing 64 of the balloon location device 42. In another example, additional or separate devices may be mounted to one or both of the sheath 12 and tissue closure device 14 as part of the method of sealing a tissue puncture. The added devices may carry the tensioner assembly. In still further arrangements, the tensioner assembly may be releasably mounted to the sheath. The tensioner assembly may be mounted to the sheath prior to or after inserting the sheath through the tissue puncture.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. An insertion sheath for use with a tissue closure system to apply a biasing force to a tissue closure device, the insertion sheath comprising:
   a sheath shaft having a central lumen;
   a hub connected to a proximal end of the sheath shaft, the hub having a retention groove, the retention groove facing radially outward from a distal end of the hub and being narrower than the sheath shaft;
   a tensioner assembly, comprising:
      a biasing member positioned on the sheath shaft and having distal and proximal end portions, the proximal end portion of the biasing member being retained to the hub in the retention groove, the biasing member being radially external to the retention groove;
      a handle member connected to the distal end portion of the biasing member, the handle member having a distal-facing lip;
      wherein applying an axial force to the distal-facing lip of the handle member against a biasing force exerted by the biasing member moves the sheath shaft axially;
      wherein the sheath comprises a constant outer diameter from the distal end portion to the proximal end portion of the biasing member.

2. The insertion sheath of claim 1, wherein the biasing member comprises a compression spring.

3. The insertion sheath of claim 1, wherein the biasing member comprises a boot structure.

4. The insertion sheath of claim 1, wherein the biasing member comprises a polymer material.

5. The insertion sheath of claim 1, wherein the proximal end portion of the biasing member is connected to the hub.

6. The insertion sheath of claim 1, wherein the handle member comprises a transparent material.

7. The insertion sheath of claim 6, wherein the sheath shaft includes indices on an outer surface thereof against which axial movement of the handle member is measured.

8. The insertion sheath of claim 1, wherein the proximal end portion of the biasing member is fixed relative to one of the sheath shaft and the hub.

9. A tissue closure sheath, comprising:
an insertion sheath, the insertion sheath comprising:
a sheath shaft having a central lumen;
a hub connected to a proximal end of the sheath shaft, the hub having a retention groove;
a tensioner assembly, comprising:
a biasing member positioned on the sheath shaft and having distal and proximal end portions, the proximal end portion being retained in the retention groove, the proximal end portion being radially external to the retention groove, wherein the sheath shaft comprises a constant outer diameter from the proximal end portion to the distal end portion of the biasing member;
a handle member connected to the distal end portion of the biasing member;
wherein applying an axial force to the handle member against a biasing force exerted by the biasing member moves the sheath shaft axially.

10. The tissue closure sheath of claim 9, wherein the biasing member comprises a compression spring.

11. The tissue closure sheath of claim 9, wherein the biasing member comprises a boot structure.

12. The tissue closure sheath of claim 9, wherein the biasing member comprises a polymer material.

13. The tissue closure sheath of claim 9, wherein the proximal end portion of the biasing member is connected to the hub.

14. The tissue closure sheath of claim 9, wherein the handle member comprises a transparent material.

15. The tissue closure sheath of claim 9, wherein the sheath shaft includes indices on an outer surface thereof against which axial movement of the handle member is measurable.

16. The tissue closure sheath of claim 9, wherein the proximal end portion of the biasing member is fixed relative to one of the sheath shaft and the hub.

17. The tissue closure sheath of claim 9, wherein the handle member includes a lip configured to apply an axial force to the handle member.

18. A tissue closure system sheath, comprising:
an insertion sheath, the insertion sheath comprising:
a sheath shaft having an axial lumen;
a hub connected to a proximal end of the sheath shaft, the hub having a retention groove extending around a distal end of the hub, the retention groove being narrower than the sheath shaft;
a tensioner assembly, comprising:
a biasing member positioned around the sheath shaft at the retention groove and having distal and proximal end portions, the biasing member being retained on the sheath shaft in a position radially external to the retention groove, wherein the sheath shaft comprises a constant outer diameter from the distal end portion to the proximal end portion of the biasing member;
a handle member connected to the distal end portion of the biasing member;
wherein applying an axial force to the handle member against a biasing force exerted by the biasing member moves the sheath shaft axially to seal a vessel puncture when an expandable member is connected to the hub and positioned extending through the axial lumen.

19. A tissue closure system sheath having a force tensioner assembly, comprising:
an insertion sheath, comprising:
a sheath shaft having a distal end, a proximal end, and an outer surface;
a hub connected to the proximal end of the sheath shaft;
a retention groove extending around the outer surface of the hub;
a plurality of indices on the outer surface of the sheath shaft;
a tensioner assembly, comprising:
a handle portion positioned around the sheath shaft of the insertion sheath external to the plurality of indices, the handle portion being movable relative to the plurality of indices;
a biasing member having a distal end and a proximal end, the distal end being connected to the handle portion, the proximal end being retained by the hub radially external to the retention groove, the sheath shaft having a constant outer diameter from the proximal end to the distal end of the biasing member.

* * * * *